(12) United States Patent
Hartung

(10) Patent No.: US 6,724,522 B2
(45) Date of Patent: Apr. 20, 2004

(54) LIGHT WAVE CONVERSION ARRANGEMENT AND METHOD FOR MAKING SAME FOR DENTAL PROCEDURES

(75) Inventor: Martin Hartung, Munich (DE)

(73) Assignee: 3M ESPE AG, Seefeld (DE)

( * ) Notice: Subject to any disclaimer, the term of this patent is extended or adjusted under 35 U.S.C. 154(b) by 125 days.

(21) Appl. No.: 09/781,960

(22) Filed: Feb. 14, 2001

(65) Prior Publication Data

US 2001/0019446 A1 Sep. 6, 2001

(30) Foreign Application Priority Data

Feb. 14, 2000 (DE) .......................... 100 06 286

(51) Int. Cl.$^7$ ............................. G02F 1/365; A61C 3/00
(52) U.S. Cl. ......................................... 359/332; 433/29
(58) Field of Search ........................... 359/326–332; 433/29

(56) References Cited

U.S. PATENT DOCUMENTS

| | | | |
|---|---|---|---|
| 4,884,860 A | * 12/1989 | Brown | 385/27 |
| 5,144,636 A | * 9/1992 | Yoshida et al. | 372/50 |
| 6,117,529 A | * 9/2000 | Leising et al. | 428/209 |
| 6,208,458 B1 | * 3/2001 | Galvanauskas et al. | 359/345 |
| 6,249,372 B1 | * 6/2001 | Kobayashi et al. | 359/326 |
| 6,333,943 B1 | * 12/2001 | Yamamoto et al. | 372/43 |
| 6,504,301 B1 | * 1/2003 | Lowery | 313/512 |

FOREIGN PATENT DOCUMENTS

| | | |
|---|---|---|
| DE | 2913415 A1 | 10/1979 |
| DE | 3523243 A1 | 1/1987 |
| DE | 3644839 A1 | 6/1988 |
| DE | 3703495 A1 | 8/1988 |
| DE | 19830335 A1 | 1/1999 |

* cited by examiner

Primary Examiner—John D. Lee
(74) Attorney, Agent, or Firm—Crowell & Moring LLP

(57) ABSTRACT

The invention relates to a light wave converter assembly, comprising a light guide and a light wave converter, comprising a converter substance, which converts a part of the incident light into light of a longer wavelength, whereby the converted light is guided together with the unconverted light through the light guide to an exit port.

27 Claims, 1 Drawing Sheet

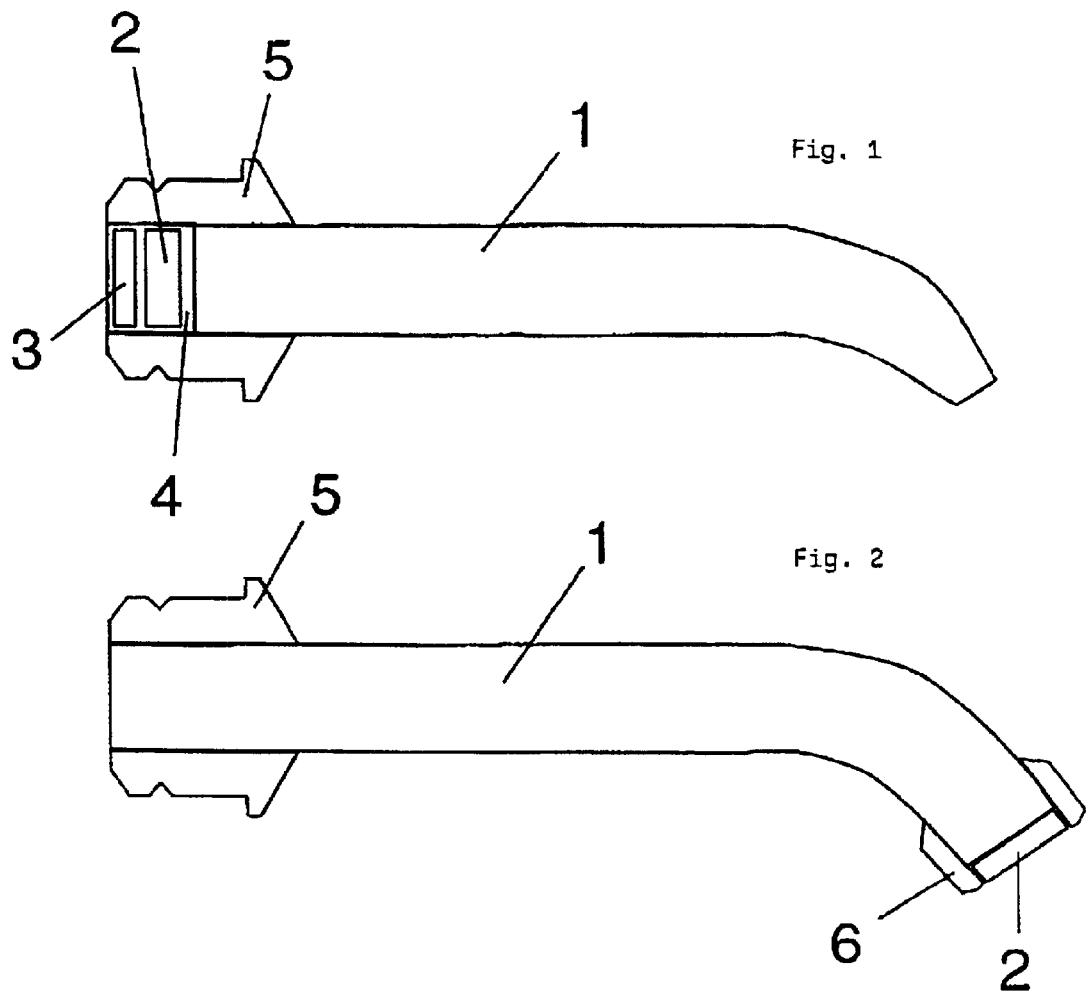

LIGHT WAVE CONVERSION ARRANGEMENT AND METHOD FOR MAKING SAME FOR DENTAL PROCEDURES

BACKGROUND AND SUMMARY OF THE INVENTION

This application claims the priority of German patent document 100 06 286.5, filed Feb. 14, 2000, the disclosure of which is expressly incorporated by reference herein.

The invention relates to a light wave converter, which partially converts incident light into light of a longer wavelength, whereby the converted light is passed together with the unconverted light through a light guide to an exit port.

There exist photopolymerization devices, which emit blue light with a wavelength ranging from approximately 400 to 500 nm. Said photopolymerization devices are used, for example, in dental practices for polymerization of the photocuring composite materials. However, the light that is optimal for polymerization is so bright that the use of these lamps is not suitable for illumination purposes in the mouth. Moreover, the blue light color, which is emitted from such devices and is required for polymerization, is suitable only for this application. For purposes, such as diagnostics, however, white light has been demonstrated to be advantageous.

Similarly there exist white light emitting operating lamps for illuminating the area to be treated. In the dental domain this light is also guided with a mirror to the area to be treated for better illumination of the individual areas. However, this procedure assumes that there is no impediment in the ray path. Moreover, the level of illumination that can be reached with this method is inadequate to transilluminate, for example, teeth, as is helpful for a dental diagnosis or for illuminating tooth defects (cracks or caries).

The German Patent Document DE A 198 30 335 discloses a fiber rod light guide for dental purposes, whose core is jacketed with a color coat. This color coat enables complete blockage of the light and prevents the dentist from being blinded by light emitted from the side of the fiber rod. Furthermore, it makes it possible to guide light, generated by polymerization devices, specifically to the spatially narrowly defined area to be treated.

The German Patent Document DE A 2913415 (corresponding U.S. Pat. No. 4,266,535) discloses a diagnostic lamp in the form of a small device or a pocket device for tooth examination for fluorescent excitation of a fluorescible material that is applied to the teeth and the gums. The diagnostic lamp comprises a filter unit, which is adapted to the fluorescible material and which is made of a dichroic and a blue color filter. The existing filters result in a significant attenuation of the light, which renders detailed examination of the object to be viewed more difficult.

The German Patent Document DE 36 44 839 A1 discloses an illuminating device, in particular for polymerization of dental plastics, which can be cured by means of light in the blue spectral range, with a liquid light guide. It is stated that the fill liquid can contain, for example, a dye, which serves as the filter, or a fluorescing dye.

An object of the present invention can be regarded as providing a device, which enables better illumination of the area to be treated. It is supposed to be easy to use and at the same time, if desired, also be bright enough at one point in order to transilluminate, for example, also the individual teeth. In this manner, hidden tooth defects, like cracks or caries, can also be detected and/or diagnosed.

This problem is solved by providing a light wave converter, optionally as an attachment for a photopolymerization device, which emits light preferably in the blue spectral range. This light wave converter is described herein and in the claims.

An object of the invention is also a process for illuminating and/or transilluminating teeth, in particular for diagnostic purposes, whereby the light wave converter converts light, which is usually generated by a polymerization lamp.

The conversion of the light incident on the device can be achieved by different methods.

Usually one part of the wavelength range of the light, penetrating into the light wave converter or the converter substance, is converted into light of a longer wavelength by luminescent processes. Through additive color mixture light with another color impression can be generated in this manner as a function of the wavelength of the penetrating light and the converter substance that is used.

However, it is also contemplated according to certain preferred embodiments of the invention that the light is divided into two or more partial beams before or after penetration into the light wave converter, whereby a partial beam is guided to the light wave converter and is converted completely into another wavelength range, whereas another partial beam is not converted and is guided past the light wave converter. In the area of the exit port of the light wave converter the converted and unconverted beams are united again. Then the light that is generated thus is guided directly or through a light guide to an exit port.

In this respect the invention exhibits the following advantages.

The photopolymerization devices of high light output that are wide spread and have been demonstrated to be reliable in dental practices can also be used in a simple manner to illuminate the area to be treated and for diagnostic purposes for transilluminating individual teeth. In contrast to the operating lamps, the light intensity can be significantly increased at one point.

Since the light can be guided over a light guide to an exit port, the light can be focused directly on the area to be treated without the need for additional mirrors. This feature makes it possible to utilize the complete intensity of the generated light of the desired wavelength.

Furthermore, through the use of a suitable converter substance light of any arbitrarily long wavelength can be generated as a function of the wavelength of the arriving beam of light without having to insert filter systems. With the spectral colors that can be coordinated over wide ranges and can be generated from the converted light with the unconverted light by additive color mixture, it is possible to adapt the light wave converter to the desired task so that for diagnostic purposes or for illuminating especially defective teeth, for example, maximum contrast can be obtained.

In principle, the incident light can exhibit any conceivable wavelength in the visible range, thus from 380 nm to approximately 700 nm. In certain preferred embodiments the incident light has a wavelength, ranging from 380 nm to 520 nm, as normally generated by dental photopolymerization devices.

The light wave converter converts preferably one part of the incident light to one or more wavelength(s), lying in the green, yellow or red spectral range. Preferred is the generation of green light, because light having the wavelength spectrum of the color white can be generated through the additive color mixture with the unconverted portion of the incident blue light.

With white light, for example, teeth can be illuminated and optionally transilluminated more effectively and contrasted more reliably than with blue light. Defects in the teeth or the fillings, for example cracks and caries, can be better visualized in this manner.

However, embodiments are also contemplated with a conversion into a wavelength range, which is matched with the substance to be illuminated and which makes it possible, optionally together with filter units, to distinguish, for example, tooth fillings having the color of the tooth from the natural tooth substance. The wavelengths can also be chosen in such a manner that the converted light initiates, for example, therapeutic chemical reactions in the oral cavity of suitable light activatable substances.

Light devices, which emit short wavelength light in the visible range, are used especially in dental practices to cure photocuring substances. Thus, the inventive light wave converter makes it possible to expand the range of application of the already existing devices. Thus, the dental offices save money and space that would be required for the additional acquisition of a device to generate white light for the described areas of application.

According to various preferred embodiments of the invention, the light wave converter can be disposed in front of, in or behind the light guide device. Also contemplated is a combination of arrangements or the use of several light wave converters at different locations. It can also be advantageous if the light wave converter is uniformly distributed, for example dispersed, in the light guide. In a preferred embodiment the light wave converter is located in the area of the entry port of the light guide.

In principle, the shape of the light guide is arbitrary, but preferably adapted to the intended application.

The light guide can be straight or curved. It is advantageous to bend said light guide at an angle of approximately 60 degrees, optionally from 90 degrees to 180 degrees, depending on the location in the mouth to be illuminated. In a preferred embodiment the light guide is flexible (goose neck lamp). This design enables an individual adaptation to the respective situation.

A small exit port with a diameter ranging from 1 to 10 mm, preferably from 2 to 5 mm, has been shown to be advantageous. It allows for a point illumination of the individual teeth and the space between the teeth.

In addition, the light wave converter can exhibit a brightness controller. The brightness is controlled preferably mechanically, for example, in the form of a diaphragm (iris or slotted aperture). Such a brightness controller enables better adjustment of the light intensity to the object to be illuminated or transilluminated, for example a tooth. To transilluminate the front teeth, far less intensity is required than for the side teeth.

Optionally the light wave converter also comprises a band pass filter, preferably a narrow-band band pass filter with a transmission, ranging from 400 to 500 nm, preferably ranging from 440 to 480 nm.

This feature makes it possible to match accurately and repeatedly the color of the light generated by the light wave converter, since experience has shown that the spectral range of the photopolymerization devices (in particular the long and short wave critical wavelengths) can vary widely from device to device. Then the light, which is defined thus in its spectral composition and guided to the wavelength converter, is totally or partially converted. Thus, the band pass filter also enables the excited light to be adjusted to the absorption spectrum of the converter substance.

The light wave converter is preferably designed interchangeably. For example, it can be achieved by means of a coupling on one end of the light wave converter. However, a shape in the form of a thread is also contemplated. Preferably a coupling, specified by the photopolymerization device, is used in order to enable a simple exchange of the light guide, which is usually mounted in the devices, for polymerization applications with the light wave converter for illumination applications.

Substances, which can be used for converting the electromagnetic waves preferably in the visible range, are all substances that can luminesce, in particular fluoresce, when optically excited.

The converter substances include organic and inorganic dyes or pigments.

Organic dyes can be selected from the class of perylenes, aldazines, thioxanthenes and/or the naphthalimides, preferably in pigment form.

Examples of such dyes are listed in the German Patent Document DE 37 03 495 A1.

Useful inorganic dyes contain preferably elements from the auxiliary groups, in particular from the group of lanthanides. Especially preferred are the elements Y, La, Ce, Pr, Nd, Sm, Yb and Lu.

The converter substance is usually used in a quantity ranging from 0.005 to 5% by weight, preferably from 0.01 to 1% by weight, based on the mass of the substance to be dyed.

Commercially available and quite suitable are, for example, Lumogen® dyes (BASF AG, Ludwigshafen) or Lumilux® pigments (Riedel de Haen GmbH, Seelze).

Contemplated embodiments for the light wave converter include converter substance-penetrated filter sheets or plates made of glass or plastic, like PMMA, PE, PP, polystyrene (PS), polycarbonate (PC), PVC; converter substance-coated substrates, like glass, crystalline filter plates made of, for example, Cer-doped YAG, like $Y_3Al_5O_{12}$:Ce or $Y_3Al_{2.5}Ga_{2.5}O_{12}$:Ce; converter substance-coated hollow bodies; the converter substance-enveloping glass fibers or glass rods, preferably in the doped form. In this respect the converter can be permanently or reversibly connected, for example in the form of an interchangeable filter disk, to the light guide.

The light wave converter can be sterilized preferably with hot steam. This sterilization can be achieved, for example, by embedding the light wave converter into a transparent or stable epoxy resin or by applying an exterior glass layer.

Other objects, advantages and novel features of the present invention will become apparent from the following detailed description of the invention when considered in conjunction with the accompanying drawings.

BRIEF DESCRIPTION OF THE DRAWINGS

FIG. 1 is a schematic sectional side view of a light wave converter, contemplated according to a preferred embodiment of the invention; and.

FIG. 2 is a schematic sectional side view of a light wave converter, contemplated according to a preferred embodiment of the invention.

DETAILED DESCRIPTION OF THE DRAWINGS

FIG. 1 depicts a light wave converter in the form of a rod that comprises an optical waveguide 1, a wavelength converter plate 2 and a band pass filter 3. The latter are cast together with the optical waveguide 1 with a transparent casting resin 4 in the coupling 5.

FIG. 2 depicts a light guide rod 1 with coupling 5, as used typically with photopolymerization devices. The wavelength converter plate 2 is fastened in a mountable cap 6.

The light wave converter, according to the invention, can be used, for example, together with dental photopolymerization devices. They emit preferably visible light in the blue spectral range. A part of the blue light is converted into light of a longer wavelength by means of the light wave converter. Through additive color mixture white light can be generated, for example, in this manner. Contemplated, however, is also any other color that can be obtained through additive color mixture. This feature makes it possible, for example, to extend the use of known photopolymerization devices to diagnostic applications.

They include the improved illumination of the area to be examined, preferably in the spectral range that is visible to the human eye.

The area to be irradiated is in particular the oral cavity and the restorative dental material, which can also be located optionally outside the oral cavity.

Furthermore, to facilitate the diagnosis, individual teeth can be thoroughly examined, for example, by transilluminating them with the generated, preferably white light, whereby cracks or caries hidden in the tooth can be better detected.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed:

1. A dental illumination or transillumination system, comprising a photopolymerization system and a light wave converter assembly with a light guide and a light wave converter,
    wherein the light wave converter exhibits a converter substance operable to convert a part of incident light into light of a longer wavelength, whereby the converted light is guided together with a portion of the unconverted light to an exit port; and the light, converted by the converter substance, together with the unconverted light yields a light with the wavelength spectrum of the color white in order to illuminate hard tooth substances.

2. The system, as claimed in claim 1, wherein the incident light exhibits a wavelength ranging from 380 to 520 nm.

3. The system, as claimed in claim 2, further comprising a band pass filter.

4. The system, as claimed in claim 1, further comprising a band pass filter.

5. The system, as claimed in claim 1, comprising a brightness controller.

6. The system, as claimed in claim 1, wherein the converter substance is chosen from substances, which, when optically excited, can luminescence.

7. The System, as claimed in claim 1, wherein the converter substance is at least one of inorganic dyes, including the auxiliary group elements and elements from the group of lanthanides, and organic dyes, including the class of perylenes, aldazines, thioxanthenes and/or naphthalimides.

8. The system, as claimed in claim 1, wherein the light guide is flexible.

9. The system, as claimed in claim 1, wherein the diameter of the exit port ranges from 1 to 10 mm.

10. The system, as claimed in claim 1, including a coupling or a thread.

11. The system, as claimed in claim 1, wherein the converter substance is present in a quantity ranging from 0.005 to 5% by weight, based on a substance to be dyed.

12. The system, as claimed in claim 1, wherein the converter assembly is a hot steam sterilized converter assembly.

13. The system, as claimed in claim 1, wherein the light wave converter exhibits one of a form of a filter disk, a glass fiber or a glass rod.

14. The illumination or transillumination system according to claim 1,
    wherein the incident light exhibits a wavelength ranging from 380 to 520 nm.

15. The illumination or transillumination system according to claim 1, wherein the incident light is generated by a polymerization lamp as a light source.

16. Process, comprising the steps: a) provision of a light wave converter assembly, comprising a light guide and a light wave converter, wherein the light wave converter exhibits a converter substance, which in use converts a part of incident light into light of a longer wavelength, and wherein the converted light is guided together with a portion of the unconverted light to an exit port, and b) connection of the light wave converter to a polymerization device, c) at least one of illumination and transillumination of hard tooth substance with light which is generated by the polymerization device and is converted by the light wave converter.

17. The process according to claim 16, wherein the incident light exhibits a wavelength ranging from 380 to 520 nm.

18. The process according to claim 16, further comprising a band pass filter.

19. The process according to claim 16, comprising a brightness controller.

20. The process according to claim 16, wherein the converter substance is chosen from substances, which, when optically excited, can luminescence.

21. The process according to claim 16, wherein the converter substance is at least one of inorganic dyes, including the auxiliary group elements and elements from the group of lanthanides, and organic dyes, including the class of perylenes, aldazines, thioxanthenes and/or napthanalimides.

22. The process according to claim 16, wherein the light guide is flexible.

23. The process according to claim 16, wherein the diameter of the exit port ranges from 1 to 10 mm.

24. The process according to claim 16, including a coupling or a thread.

25. The process according to claim 16, wherein the converter substance is present in a quantity ranging from 0.0005 to 5% by weight, based on a substance to be dyed.

26. The process according to claim 16, wherein the converter assembly is a hot stream sterilized converter assembly.

27. The process according to claim 16, wherein the light wave converter exhibits one of a form of a filter disk, a glass fiber or a glass rod.

\* \* \* \* \*

UNITED STATES PATENT AND TRADEMARK OFFICE
CERTIFICATE OF CORRECTION

PATENT NO.   : 6,724,522 B2
DATED        : April 20, 2004
INVENTOR(S)  : Hartung, Martin G.

It is certified that error appears in the above-identified patent and that said Letters Patent is hereby corrected as shown below:

<u>Column 6,</u>
Lines 49-50, "napthanalimides" and insert -- naphthalimides --, therefor.

Signed and Sealed this

Twenty-third Day of August, 2005

JON W. DUDAS
*Director of the United States Patent and Trademark Office*